United States Patent
Luchi et al.

(10) Patent No.: US 8,410,304 B2
(45) Date of Patent: *Apr. 2, 2013

(54) PROCESS FOR PREPARING GAMMA-HYDROXYBUTYRATE

(75) Inventors: James Luchi, Upland, CA (US); Daniel Levin, La Canada, CA (US)

(73) Assignee: Norac Pharma, Azusa, CA (US)

( * ) Notice: Subject to any disclaimer, the term of this patent is extended or adjusted under 35 U.S.C. 154(b) by 105 days.

This patent is subject to a terminal disclaimer.

(21) Appl. No.: 12/905,767

(22) Filed: Oct. 15, 2010

(65) Prior Publication Data

US 2011/0034727 A1 Feb. 10, 2011

Related U.S. Application Data

(60) Provisional application No. 61/254,644, filed on Oct. 23, 2009.

(51) Int. Cl.
*C07C 69/66* (2006.01)
(52) U.S. Cl. ........................ 560/179
(58) Field of Classification Search .......... None
See application file for complete search history.

(56) References Cited

U.S. PATENT DOCUMENTS

| | | | | |
|---|---|---|---|---|
| 3,051,619 A | * | 8/1962 | Laborit | 514/461 |
| 3,166,574 A | | 1/1965 | Gensheimer et al. | |
| 3,878,029 A | * | 4/1975 | Baird et al. | 159/6.3 |
| 4,173,246 A | * | 11/1979 | Nunlist et al. | 159/6.2 |
| 4,393,236 A | * | 7/1983 | Klosa | 562/579 |
| 5,789,603 A | | 8/1998 | Koehler et al. | |
| 6,472,431 B2 | | 10/2002 | Cook et al. | |
| 6,752,529 B2 | * | 6/2004 | Holl | 366/279 |
| 6,780,889 B2 | | 8/2004 | Cook et al. | |
| 7,125,527 B2 | | 10/2006 | Holl | |
| 7,165,881 B2 | | 1/2007 | Holl | |
| 7,262,219 B2 | | 8/2007 | Cook et al. | |
| 2003/0043690 A1 | | 3/2003 | Holl | |
| 2005/0077034 A1 | * | 4/2005 | King | 165/163 |
| 2006/0286015 A1 | | 12/2006 | Holl | |
| 2007/0270491 A1 | | 11/2007 | Cook et al. | |
| 2011/0028551 A1 | | 2/2011 | Levin et al. | |
| 2011/0034727 A1 | | 2/2011 | Luchi et al. | |

FOREIGN PATENT DOCUMENTS

| | | |
|---|---|---|
| DE | 237308 | 7/1986 |
| DE | 237309 | 7/1986 |
| DE | 237310 | 7/1986 |
| WO | 2006124609 | 11/2006 |
| WO | 2009129350 A2 | 10/2009 |

OTHER PUBLICATIONS

Marvel et al., JACS, 1929; 51, 260-262.*
Hampton et al., Organic Process Research & Development 2008, 12, 946-949.*
Young, Lee; International Search Report and Written Opinion from corresponding International Patent Application No. PCT/US2011/056242; Mar. 6, 2012; United States Patent and Trademark Office as ISA; pp. 1-8.
Marvel et al., The Preparation of the Sodium Salts of Omega-Hydroxybutyric, -Valeric and -Caproic Acids; Journal of the American Chemical Society; 1929; 51, 260-262.

(Continued)

*Primary Examiner* — Karl J Puttlitz

(57) ABSTRACT

Disclosed herein are processes for preparing aqueous γ-hydroxybutyrate having a pH of about 8 or less (upon reaching equilibrium). The disclosed processes include both continuous processes and batch processes wherein the ratio of reactants is controlled to provide the product at the desired pH.

33 Claims, 3 Drawing Sheets

OTHER PUBLICATIONS

Hampton et al., Continuous organic Synthesis in a Spinning Tube-in-Tube Reactor: TEMPO-Catalyzed Oxidation of Alcohols by Hypochlorite; Organic Process Research and Development, 2008, 12, 946-949.

Gonzalez et al., High Conversion, Solvent Free, Continuous Synthesis of Imidazolium Ionic Liquids in Spinning Tube-in-Tube Reactors; Organic Process Research and Development; 2008, 13, 64-66.

La Cioliono et al., The chemical interconversion of GHB and GBL; forensic issues and implications, Journal of Forensic Sciences, 1315-1323, 2001.

Peterson, Birgitta, Utveckling av en LC-MS-metod för analys av gamma-hydroxibutyrat, gamma-butyrolakton, 1,4-butandiol, amfetamin och metadon, Jun. 1, 2007 (abstract in English).

Page et al., "An Interactive Lesson in Acid/Base and Pro-Drug Chemistry Using Sodium Gamma-Hydroxybutyrate and Commercial Test Coasters", American Journal of Pharmaceutical Education, 2007; 71(3) Article 54.

Kim, Su Mi; PCT International Search Report, Korean Intellectual Property Office, Oct. 22, 2009; p. 1-3; Korea.

* cited by examiner

PROCESS FOR PREPARING GAMMA-HYDROXYBUTYRATE

CROSS-REFERENCE TO RELATED APPLICATIONS

This application claims the benefit of priority of U.S. Provisional Application No. 61/254,644, filed Oct. 23, 2009; the entire contents of which are incorporated herein by reference.

BACKGROUND

γ-hydroxybutyrates (GHBs), such as sodium γ-hydroxybutyrate (NaGHB, also known as sodium oxybate) and γ-hydroxybutyric acids, are used therapeutically to treat insomnia, depression, narcolepsy, and alcoholism, and are also used as anesthetics and hypnotics. GHBs are FDA approved to reduce the number of cataplexy attacks in patients with narcolepsy. For this treatment, NaGHB is typically administered as an oral solution containing about 0.5 g/mL NaGHB with a dosage range from 4.5 g per night to 9 g per night.

NaGHB is generally prepared by reacting γ-butyrolactone (GBL) with sodium hydroxide, typically under reflux conditions in an aqueous solution. (See, e.g., JACS1929, v. 51, p. 260). Established methods for preparing NaGHB typically result in only moderate yields, require extended reaction times, and/or require further recrystallization or processing steps. For example, U.S. Pat. No. 3,051,619 describes a process for preparing aqueous compositions of NaGHB involving prolonged heating of an aqueous mixture of GBL and NaOH, followed by subsequent recrystallization of NaGHB from alcohol.

German Pat. Nos. DD 237,308-237,310 describe the synthesis of NaGHB in water or water/alcohol mixtures by prolonged heating of an aqueous mixture of sodium hydroxide and GBL. While the use of alcohol/water mixtures avoids the additional recrystallization step, the process results in significantly less than quantitative yield, requires an alcohol wash of the product, and requires an evaporation/distillation step before the final product is isolated.

NaGHB drug products are typically formulated as an aqueous solution at or around neutral pH. Processes for preparing NaGHB drug formulations, however, require an additional pH adjustment step, after the initial preparation of an aqueous solution of NaGHB. For example, U.S. Pat. Nos. 6,472,431, 6,780,889, 7,262,219, and U.S. Patent Application Publication No. 20070270491, all to Cook et al., describe formulating solid NaGHB as a drug product by dissolving the solid in water, which results in a high pH solution, followed by adjusting the pH of the solution by addition of an acid to give an approximately neutral pH drug product.

SUMMARY

The processes described herein are useful for preparing γ-hydroxybutyrates in high yield while avoiding prolonged heating of the reaction mixture of γ-butyrolactone (GBL) and metal hydroxide. The processes also result in aqueous solutions of γ-hydroxybutyrate that do not require further pH adjustment prior to or during formulation, i.e., the product solution (upon reaching equilibrium) is at a pH of about 8 or less, preferably from about 6 to about 8, and more preferably from about 7 to about 8. The resulting aqueous solutions can thus be used directly in drug product formulations without the need for further pH adjustment.

The continuous process for preparing γ-hydroxybutyrate comprises: (a) continuously feeding a first feedstock of γ-butyrolactone and a second feedstock of aqueous metal hydroxide into a reaction zone, at relative rates sufficient to maintain about 1 equivalent or less of metal hydroxide, relative to γ-butyrolactone, in the reaction zone; (b) continuously reacting the γ-butyrolactone and the metal hydroxide in the reaction zone to form aqueous γ-hydroxybutyrate; and (c) continuously discharging the aqueous γ-hydroxybutyrate from the reaction zone.

Another continuous process described herein for preparing γ-hydroxybutyrate comprises (a) continuously feeding a first feedstock of γ-butyrolactone and a second feedstock of aqueous metal hydroxide containing about 1 equivalent or less of metal hydroxide, relative to γ-butyrolactone, into a reaction zone; (b) continuously reacting the γ-butyrolactone and the metal hydroxide in the reaction zone to form aqueous γ-hydroxybutyrate; and (c) continuously discharging the aqueous γ-hydroxybutyrate from the reaction zone.

The batch process for preparing γ-hydroxybutyrate comprises: reacting a metal hydroxide with γ-butyrolactone by slowly mixing about 1 equivalent or less of aqueous metal hydroxide with γ-butyrolactone, to form aqueous γ-hydroxybutyrate.

DETAILED DESCRIPTION

The processes disclosed herein react γ-butyrolactone with metal hydroxide in a reaction medium to provide aqueous γ-hydroxybutyrate. The reaction proceeds by hydrolysis of γ-butyrolactone by the metal hydroxide to provide the desired metal salt of γ-hydroxybutyrate, according to the following scheme.

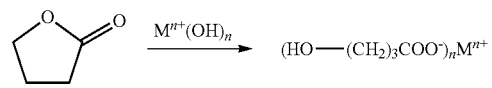

A variety of metal hydroxides ($M^{n+}(OH)_n$) are suitable for use with the processes, including, without limitation, alkali metal hydroxides (wherein n is 1, i.e., MOH), such as sodium, potassium, rubidium, or caesium hydroxide; alkaline earth metal hydroxides (wherein n is 2, i.e., $M(OH)_2$), such as beryllium, magnesium, calcium, strontium, barium, or radium hydroxide; and other metal hydroxides (wherein n is 1-4, and preferably 1-2), such as basic transition metal hydroxides. Preferably, the metal hydroxide is an alkali metal hydroxide, such as sodium hydroxide, potassium hydroxide, rubidium hydroxide, caesium hydroxide, or a combination thereof. Sodium hydroxide is most preferred. The hydroxide used as the base will result in a corresponding γ-hydroxybutyrate having a metal cation ($M^{n+}$), e.g., sodium γ-hydroxybutyrate.

As briefly discussed above, the processes described herein are useful for preparing approximately neutral pH solutions of γ-hydroxbutyrate (upon reaching equilibrium). By directly preparing solutions of γ-hydroxybutyrate within the desired pH range, the processes also avoid the need for isolation of the solid γ-hydroxybutyrate, followed by redissolution of the γ-hydroxybutyrate in water and subsequent pH adjustment.

The desired pH range of the product solution (upon reaching equilibrium) is achieved in the continuous process by controlling the ratio of the metal hydroxide and γ-butyrolactone via flow rate and/or concentration adjustments. As discussed below, by selecting reactant ratio, temperatures, flow rates, and concentrations of the reactant solutions and process streams in the continuous process, about 1 equivalent or less of the metal hydroxide, relative to γ-butyrolactone, can be maintained in the reaction zone. Similarly, in the batch process, about 1 equivalent or less of metal hydroxide, relative to γ-butyrolactone, is used to prepare γ-hydroxybutyrate. The resulting γ-hydroxybutyrate, upon reaching equilibrium, has a pH within the desired range. When the product solution is referred to as at "equilibrium," this means that the solution has a stable pH, and more specifically that the pH remains constant ±0.1 pH unit over time.

Figure 1:
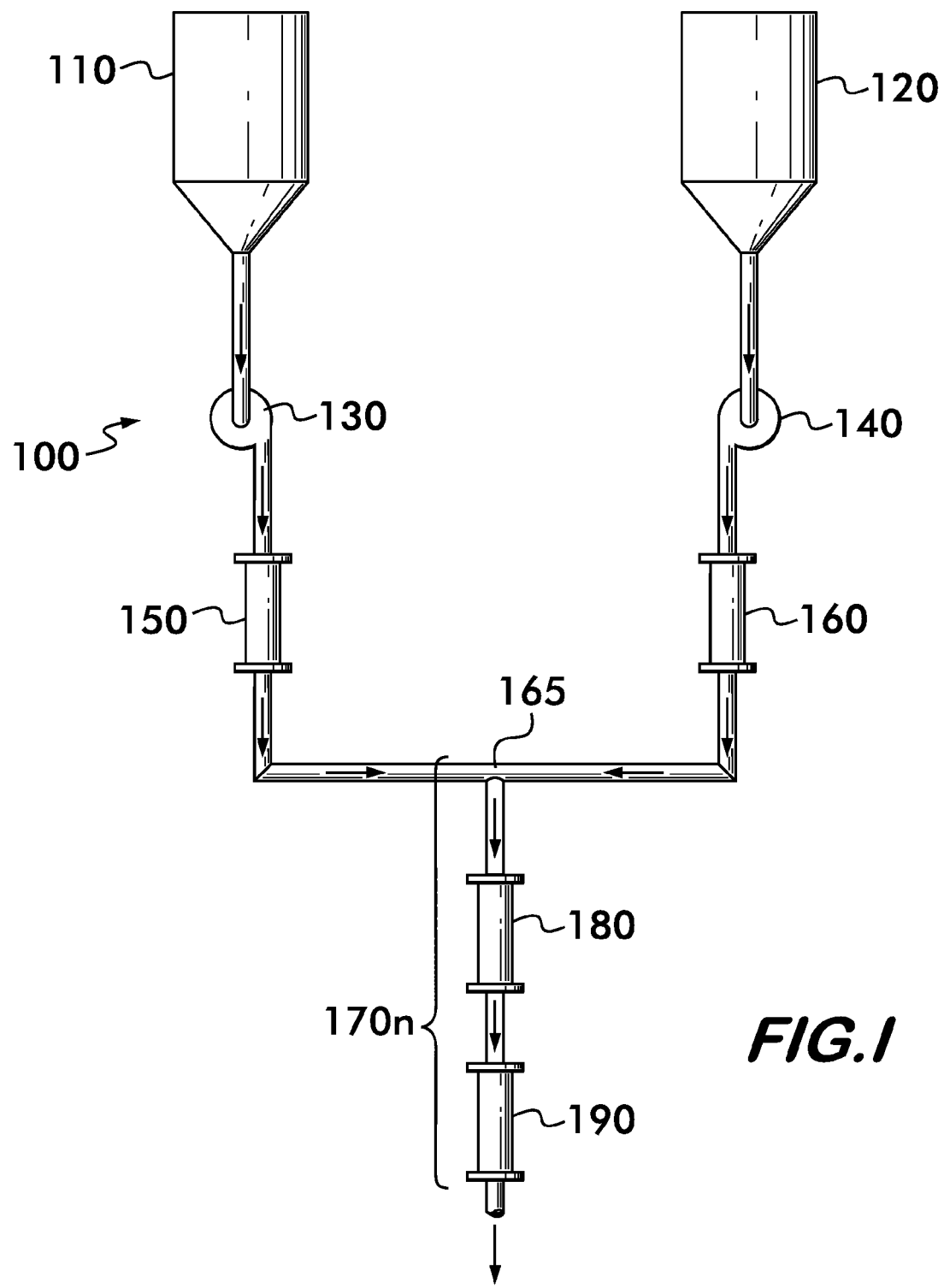
FIG. 1 is a schematic of a reactor used to carry out the continuous process for preparing γ-hydroxybutyrate.

Referring now to FIG. 1, the continuous process for preparing γ-hydroxybutyrate is carried out in a continuous process reactor 100. The feedstock of γ-butyrolactone is held in feed tank 110, and the feedstock of aqueous metal hydroxide is held in feed tank 120. The feedstock of γ-butyrolactone can be neat γ-butyrolactone or a solution or mixture of γ-butyrolactone in water. The aqueous metal hydroxide is preferably an aqueous solution, but may contain metal hydroxide dispersed in water. The feedstocks are pumped via peristaltic pumps 130 and 140 into jacketed static mixers 150 and 160, which cool and agitate the feedstocks. The feedstocks then combine at junction 165 to enter reaction zone 170n, where they react and pass through jacketed static mixers 180 and 190. The aqueous γ-hydroxybutyrate, which can be a solution or dispersion, is then discharged from reaction zone 170n into a receiving vessel (not shown) or optionally directly into a further concentrating process, an example of which is discussed with reference to FIG. 3.

The γ-butyrolactone is added as neat γ-butyrolactone to feed tank 110, or is prepared as aqueous γ-butyrolactone in feed tank 110, or in another vessel and subsequently added to feed tank 110, by mixing neat γ-butyrolactone with water. The aqueous γ-butyrolactone is allowed to equilibrate, or equilibrated through heating or cooling, if desired. The aqueous metal hydroxide is similarly prepared in feed tank 120, or in another vessel and subsequently added to feed tank 120, by mixing solid or concentrated aqueous metal hydroxide with water. Preparation of the metal hydroxide solution is exothermic, and thus the solution can be cooled or allowed to cool to room temperature, as desired. Feed tanks 110 or 120 can include a stirring, mixing mechanism, and/or cooling mechanism (not shown) if the aqueous mixture or solution is prepared and/or cooled in the feed tank itself.

The feedstocks are pumped from feed tanks 110 and 120 through reactor 100 by peristaltic pumps 130 and 140. Although only one pump (130 and 140) for each stream of solution is shown, other pumps can be used here or at any point in the process stream, in place of or in addition to peristaltic pumps 130 and 140. The pumps need not be peristaltic pumps, as a variety of fluid pumps can be used. The flow rates of the solutions through pumps 130 and 140 are set based on the concentration of the solutions in tanks 110 and 120. As discussed in more detail below, the flow rates and concentrations of the solutions in feed tanks 110 and 120 are used to maintain a relative ratio of about 1 equivalent or less of metal hydroxide, relative to γ-butyrolactone, in reaction zone 170n.

Prior to mixing the two solutions at junction 165 and initiating the reaction between γ-butyrolactone and metal hydroxide, the solutions are cooled by feeding the solutions through jacketed static mixers 150 and 160. The static mixers (150, 160) shown include alternating split helical mixing elements, which are non-movable, but nonetheless agitate the feedstocks as they pass through the helical mixing elements. To cool the solutions, static mixers 150 and 160 are surrounded by jackets through which chilled fluid flows. The jackets function to transfer heat from the feedstocks to the fluid in the jacket, thereby cooling the feedstocks. The feedstocks are cooled to a temperature no lower than the freezing point of the feedstock to maintain fluidity, and preferably no lower than 1 to 5° C. above the freezing point, but below room temperature, to avoid undesired heat buildup as the two reagents mix and react in reaction zone 170n. The jacket temperature of static mixers 150 and 160 is typically kept at about 0° C.

While jacketed static mixers 150 and 160 are shown, any suitable type of mixing and/or cooling device can be used in the process stream, in place of or in addition to jacketed static mixers. Such a device can contain mixing components, either active or static, which mix the solutions, including high-shear mixers, such as an STT (Spinning Tube-in-Tube), SYNTHATRON, ERGATRON, or similar high-shear mixing device. High shear mixer systems are described, for example, in Hampton, P. D., Whealon, M. D., Roberts, L. M., Yaeger, A. A., Boydson, R., Organic Process Research & Development (2008), 12, 946-949; Organic Process Research & Development (2009), 13, 64-66; U.S. Pat. No. 7,125,527, International Patent Publication No. WO2005/025732 and U.S. Patent Publication No. US2006/0286015, International Patent Publication No. WO2004/025260, U.S. Pat. No. 6,752,529, U.S. Pat. No. 7,165,881, and U.S. Patent Publication No. US2003/0043690.

Although cooling the feedstocks within the process stream is convenient, it is not essential. Thus, static mixers 150 and 160 or other mixers can be omitted from the reactor altogether. The process can be carried out by feeding pre-cooled feedstocks directly into the reaction zone. For example, the feedstocks can be pre-cooled, added to tanks 110 and 120, and fed directly into reaction zone 170n, or the feedstocks can be cooled in tanks 110 and 120 themselves, for example by using a jacketed tank, or by the use of cooling coils (not shown) positioned within tanks 110 and/or 120 through which fluid is circulated. The jacket around and/or cooling coils within tank 110 and/or 120 can be kept at about 0° C.

The feedstocks of γ-butyrolactone and metal hydroxide combine at junction 165 and react in reaction zone 170n to produce aqueous γ-hydroxybutyrate product. Junction 165 can be a simple junction where the two solutions combine or can include a jacketed or otherwise temperature controlled static or dynamic mixer (not shown), such as those discussed above. The reaction temperature in reaction zone 170n (i.e., the temperature of the reaction mixture in reaction zone 170n) is kept at 100° C. or less, and preferably at 65° C. or less, and is monitored by one or more temperature probes (not shown).

One way to maintain the reaction temperature in reaction zone 170n is through jacketed static mixers 180 and 190. Static mixers 180 and 190 include alternating split helical mixing elements, which are non-movable. The static mixers 180 and 190 are surrounded by jackets through which chilled or heated fluid flows. The jackets function to transfer heat from the solutions to the fluid in the jacket, or vice versa, thereby maintaining the temperature of the reaction stream. In reaction zone 170n, n refers to the number of static or dynamic mixers or reactors present in the zone. Thus, in this instance, n=2.

Heat transfer fluid flowing through the jacket of static mixer 180 and 190 can be concurrently (i.e., the same direction as the reaction stream), countercurrently (i.e., opposite the direction of the reaction stream), or transversely (i.e. perpendicular to the direction of the reaction stream) flowed. Preferably, heat transfer fluid flowing through the jacket of static mixer 180 is concurrently flowed, while fluid flowing through the jacket of static mixer 190 is countercurrently flowed. By controlling the temperature of the fluid in the jacket, the jacket of static mixer 180 is kept in the range of about 15 to about 35° C., and preferably at about 25° C., while the jacket of static mixer 190 is kept in the range of about 45 to about 65° C., and preferably at about 55° C.

The temperature in reaction zone 170n (i.e., the temperature of the reaction medium in reaction zone 170n) can be controlled through other means, aside from jacketed static mixers 180 and 190 shown in FIG. 1. The heating or cooling means in the reaction zone can vary widely, and can include any type of heating or cooling mechanism, such as jacketed mixers or mixers that can be heated or cooled by a piezoelectric mechanism. The reaction zone 170n can include other mixers or reactors that can be temperature regulated, in place of or in addition to static mixers 180 and 190, including any of those mixers discussed above. Multiple mixers in series are advantageously used at an increasing temperature gradient as the process flows downstream. Multiple mixers in parallel can also be used advantageously throughout reaction zone 170n in order to increase throughput. Reaction zone 170n can include one or more of such mixers (i.e., n is at least 1). The temperature in reaction zone 170n is controlled within the series of mixers by adjusting the temperature of the heat-transfer mechanism on each mixer (e.g., a heat-transfer jacket through which fluid can flow) such that downstream mixers (those closer to the end of the reaction zone) are held at a higher temperature than the prior mixer(s).

Other examples of devices that can be used in reaction zone 170n, in place of or in addition to jacketed static mixers 180 and 190, include a variety of devices that contain mixing components, either active or static, which mix the solutions, including high-shear mixers, such as an STT (Spinning Tube-in-Tube), SYNTHATRON, ERGATRON, or similar high-shear mixing device. High shear mixer systems are described, for example, in Hampton, P. D., Whealon, M. D., Roberts, L. M., Yaeger, A. A., Boydson, R., Organic Process Research & Development (2008), 12, 946-949; Organic Process Research & Development (2009), 13, 64-66; U.S. Pat. No. 7,125,527, International Patent Publication No. WO2005/025732 and U.S. Patent Publication No. US2006/0286015, International Patent Publication No. WO2004/025260, U.S. Pat. No. 6,752,529, U.S. Pat. No. 7,165,881, and U.S. Patent Publication No. US2003/0043690.

The feedstocks are fed into reaction zone 170n at relative rates sufficient to provide aqueous γ-hydroxbutyrate having a pH of about 8 or less, preferably from about 6 to about 8, and more preferably from about 7 to about 8 (upon reaching equilibrium). The desired pH of the product is achieved by adjusting the relative ratios of γ-butyrolactone to metal hydroxide via the flow rates and/or concentrations of the feedstocks to maintain a molar equivalence, and preferably a slight molar deficiency, of metal hydroxide, relative to γ-butyrolactone. The flow rates of the feedstocks are determined based on the relative concentration of γ-butyrolactone and metal hydroxide in tanks 110 and 120, and are set or adjusted to provide a molar equivalence, and preferably a slight molar deficiency, of metal hydroxide, relative to γ-butyrolactone, in reaction zone 170n.

The relative ratio of metal hydroxide and γ-butyrolactone (GBL) in reaction zone 170n is calculated according to equation (1). Equivalents of metal hydroxide relative to γ-butyrolactone equals the molar flow rate of metal hydroxide (mol/min) divided by the molar flow rate of γ-butyrolactone (mol/min). Thus, if the molar flow rates of each feedstock solution are equal, about 1 equivalent of metal hydroxide, relative to γ-butyrolactone, will be maintained in the reaction zone. More preferably, the molar flow rate of metal hydroxide is maintained at a slightly lower rate than the molar flow rate of γ-butyrolactone, to maintain a slight molar deficiency.

$$\frac{\text{mol metal hydroxide}}{\text{mol } GBL} = \frac{\text{metal hydroxide flow rate(mol/min)}}{GBL \text{ flow rate(mol/min)}} \quad (1)$$

Molar flow rates of the metal hydroxide and γ-butyrolactone are calculated according to equation (2). As can be seen from equation (2), molar flow rate (mol/min) and hence reactant ratio within reaction zone 170n can be adjusted and controlled by feedstock concentration, feedstock flow rate (mL/min), or both.

$$\text{Flow rate(mol/min)} = \frac{[\text{Feedstock}](\text{mol}/L) \times \text{flow rate(mL/min)}}{1000 \text{ mL/min}} \quad (2)$$

As an example, if tank 120 contains about 1 molar equivalent of metal hydroxide, relative to the γ-butyrolactone in tank 110, then the aqueous metal hydroxide is fed into reaction zone 170n at a rate that is from 90 to 98%, and preferably about 95%, of the flow rate of the γ-butyrolactone, to maintain a slight molar deficiency of metal hydroxide, relative to γ-butyrolactone, in the reaction zone. The flow-rates of the two solutions from tanks 110 and 120 are controlled by peristaltic pumps 130 and 140. A specific calculation using equations (1) and (2) is shown below in Example 1.

About 0.8 to about 1 equivalent of metal hydroxide, and preferably about 0.9 to about 0.98 equivalents, relative to γ-butyrolactone, is typically maintained in reaction zone 170n. Flow rates and/or concentrations for a particular reactant ratio can be determined based on equations (1) and (2) and can also be adjusted based on the pH of the product solution exiting reaction zone 170n, or based on the pH of the reaction mixture as it exits static mixer 180 or 190. pH and temperature probes directly after static mixers 180 and 190 can be used to measure the pH and temperature of the reaction mixture.

The product is continuously discharged from reaction zone 170n and can exit reactor 100 and flow into a holding tank or an overflow or other reactor (not shown) where the product solution is optionally allowed to equilibrate. The product solution can also exit reaction zone 170n or the holding tank or overflow reactor (not shown) and be fed directly into the concentration process discussed with reference to FIG. 3. After exiting reaction zone 170n and after optional concentration, the pH of the aqueous γ-hydroxybutyrate is as desired, less than about pH 8, preferably from pH about 6 to about pH 8, and more preferably from about 7 to about 8 (upon reaching equilibrium). The continuous process does not require and typically does not involve a pH adjustment or acid/base addition, subsequent to the preparation of the aqueous γ-hydroxybutyrate, to achieve the desired pH range.

Figure 2:
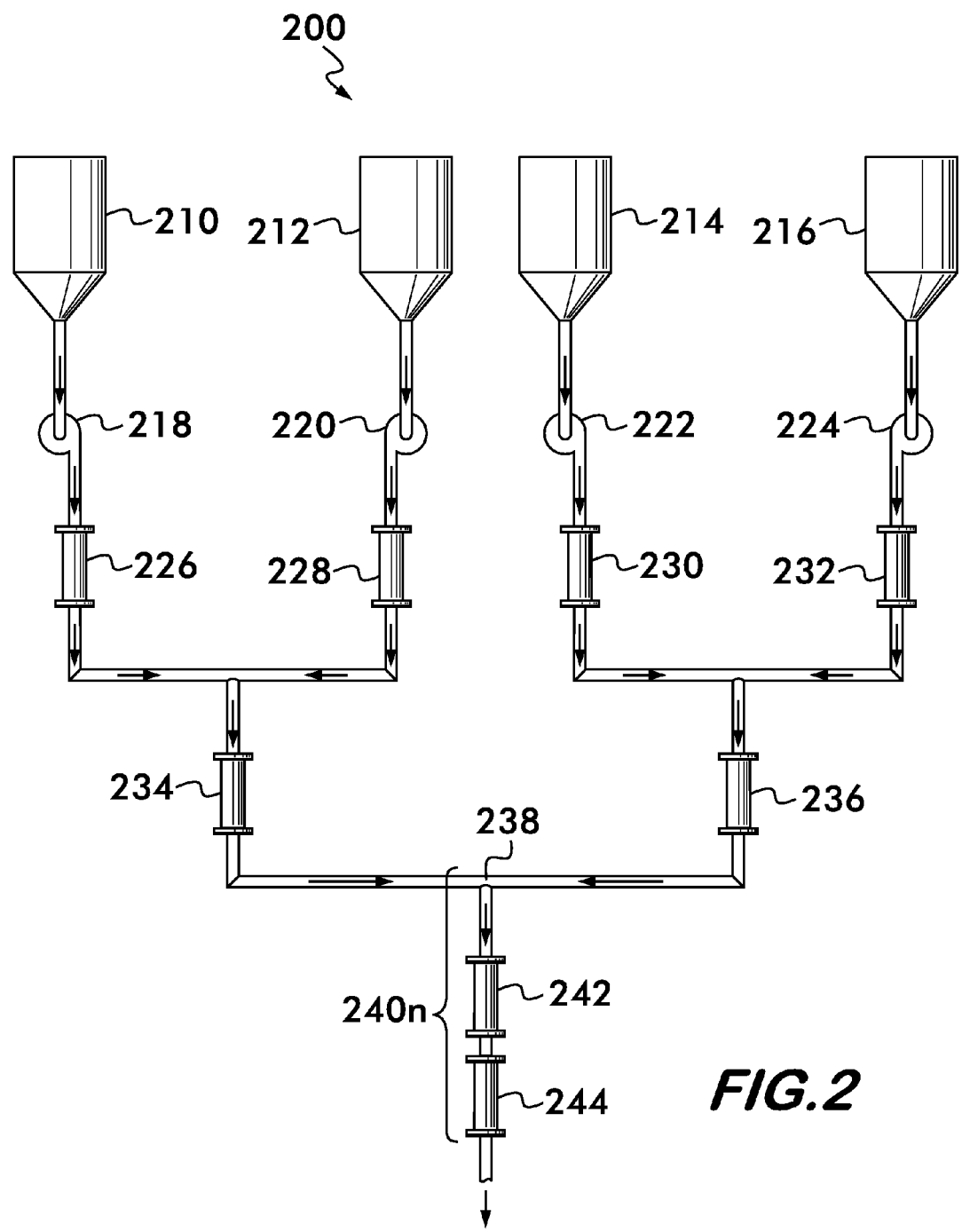
FIG. 2 is a schematic of an additional embodiment of a reactor used to carry out the continuous process for preparing γ-hydroxybutyrate.

Preparing the feedstocks of γ-hydroxybutyrate and metal hydroxide can be part of the continuous process itself. With reference to FIG. 2, a reactor 200 can include four feed tanks. Feed tanks 210 and 212 can hold neat or concentrated γ-butyrolactone and water, respectively, while feed tanks 214 and 216 hold concentrated metal hydroxide and water, respectively. Alternatively, the reactor can have a tank for neat or concentrated γ-butyrolactone, a tank for the metal hydroxide, and a common water tank, which can be used to dilute one or both feedstocks.

The γ-butyrolactone in tank 210 and water in tank 112 are pumped via peristaltic pumps 218 and 220, respectively, into optional jacketed static mixers 226 and 228, which are used to cool the water and γ-butyrolactone, as desired. As discussed above, one or more other pumps, which can be peristaltic or another type of fluid pump, can be used in place of or in addition to peristaltic pumps 218 and 220, at any point in the process stream. Similarly, various other types of mixers can be used in the process stream, in place of or in addition to any of the static mixers shown.

The γ-butyrolactone from tank 210 and water from tank 212 then combine, after exiting optional pre-cooling jacketed static mixers 226 and 228 and mix. Again, if desired, an additional jacketed static mixer 234 can be used to cool the resulting feedstock to no lower than its freezing point, and preferably from 1 to 5° C. above the freezing point, but below room temperature, prior to reacting the feedstocks. The concentrated metal hydroxide in tank 214 and water in tank 216 is similarly pumped via peristaltic pumps 222 and 224 into optional jacketed static mixers 230 and 232. After the metal hydroxide feedstock is prepared, it can optionally be cooled by an additional jacketed static mixer 236.

At this point, the process proceeds as described with reference to FIG. 1. The resulting feedstocks of metal hydroxide and γ-butyrolactone mix at junction 238 and react in reaction zone 240n wherein the reaction temperature (i.e., the temperature of the reaction medium) is kept at 100° C. or less, and preferably at 65° C. or less, for example through the use of jacketed static mixers 242 and 244 (i.e., n=2), which are in series and kept at an increasing temperature gradient. After the exiting reaction zone 240n, the γ-hydroxbutyrate product is discharged from the reaction zone, and can be held in a holding tank or overflow reactor (not shown), or fed into a further concentrating process. Upon reaching equilibration, the product solution has a pH of about 8 or less, preferably from about 6 to about 8, and more preferably from about 7 to about 8. As discussed above, the continuous process does not require and typically does not involve a pH adjustment or acid/base addition, subsequent to the preparation of the aqueous γ-hydroxybutyrate, to achieve the desired pH range.

Figure 3:
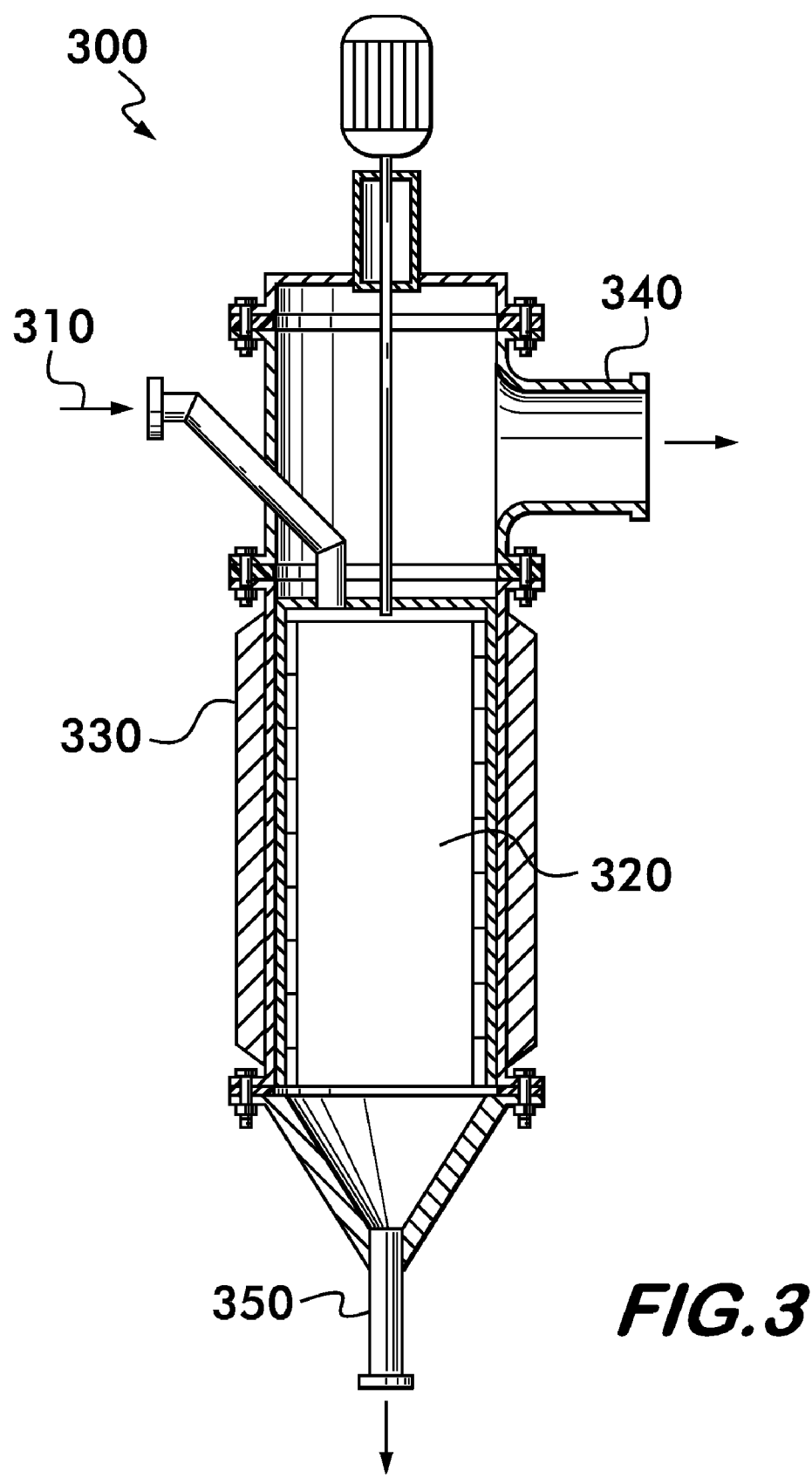
FIG. 3 is a schematic of a short path evaporator used to optionally concentrate the aqueous γ-hydroxybutyrate.

Referring now to FIG. 3, the aqueous γ-hydroxybutyrate product that exits the reaction zone can be fed directly or continuously (or fed from a holding tank or overflow reactor) into a concentrating process using a short path evaporator, such as a wiped film evaporator 300. The product solution is fed into the evaporator 300 through feed line 310, which can be directly connected to the process stream output line from the continuous process reactor, if desired. The product solution then enters evaporation chamber 320 and is subjected to wiped film evaporation by being spread via wipers into a thin film on the inner surface of the evaporation chamber 320, which is heated through heating jacket 330 and maintained at or below atmospheric pressure by a vacuum pump or other suitable pressure-reducing system, while vapors (water vapors) exit the evaporator from exit port 340. The resulting concentrated solution of γ-hydroxybutyrate exits the evaporator through exit tube 350. The residence time and/or heat used during the concentrating process can be used to drive the product solution to final equilibrium.

The concentrating process is used to concentrate the product solution to up to about 67 weight %, or higher, including even completely drying the product to a solid, by using a drying process, for example. For aqueous product solutions of γ-hydroxybutyrate, the solution is preferably concentrated up to the solubility limit of γ-hydroxybutyrate at a particular pH. For example, at a pH of from about 6 to about 8, the solution is concentrated to above about 35 weight % and up to about 55 weight %, preferably up to about 53 weight %. In other examples, the solution of γ-hydroxybutyrate is concentrated to about 40 to 45 weight %, at a pH of from about 6 to about 8.

Wiped film evaporation is desirable inasmuch as the evaporator can easily be incorporated into the continuous process (or batch process). However, a variety of other concentrating processes can be used, which can be incorporated into the continuous or batch process, or which can be carried out after the completion of the continuous reaction process as an additional step. Examples of such processes include a variety of other short path evaporation methods. The product solution can even be dried, for example, by spray drying, freeze drying or lyophilization, or azeotropic drying.

The continuous process discussed above can be carried out in a variety of other reactor designs, which include, but are not limited to, continuous stirred tank or overflow reactors, cascaded series of reactors, continuous or plug flow reactors, or a combination of such reactors. Generally, the process is one in which the reactant solutions are continuously fed into a reaction zone, while product continuously exits the reaction zone. That is, at some point in the process, reactant is continuously being fed into the reaction zone, while product is simultaneously and continuously being discharged from the reaction zone. Likewise, reactants can be continuously fed into the reaction zone, while product is continuously and simultaneously being discharged from the reaction zone, and while the product solution is continuously and simultaneously being concentrated by evaporation or other means.

The batch process of the invention is similar to the continuous in that the process is suitable for preparing aqueous solutions of γ-hydroxybutyrate having a pH of about 8 or less, preferably from about 6 to about 8, and more preferably from about 7 to about 8. In the batch process, the metal hydroxide is reacted with γ-butyrolactone by slowly mixing about 1 equivalent or less of metal hydroxide, relative to γ-butyrolactone, in an aqueous solution with γ-butyrolactone, which can be neat or as a solution or dispersion, while maintaining a reaction temperature (i.e., the temperature of the reaction medium) of 100° C. or less, and preferably 65° C. or less, to form an aqueous solution of γ-hydroxybutyrate.

The metal hydroxide is slowly mixed with the γ-butyrolactone to avoid unwanted heat build-up, and to ensure that a reaction temperature of 100° C. or less, and preferably 65° C. or less, can be maintained. Preferably, the metal hydroxide is slowly added to the γ-butyrolactone. The time period at which the metal hydroxide is slowly added is determined (and adjusted as necessary) based on the temperature in the reaction medium, which is measured with a temperature probe. If the temperature starts to rise to close to 100° C., and more preferably close to 65° C., the rate at which the metal hydroxide is added can be reduced.

The batch reaction is carried out in a suitable reaction vessel, such as a jacketed glass reactor. The jacket temperature can be used to maintain the temperature of the reaction medium. For example, when adding about a 7 M solution of metal hydroxide to a slightly more concentrated solution of γ-butyrolactone of roughly equivalent volume over a period of about 2 hours, the jacket temperature of the jacketed glass reactor can be maintained at 55±5° C., to ensure that the reaction medium does not rise above 100° C., and preferably 65° C. In this instance, the reaction mixture is maintained about from about 50 to about 60° C.

About 1 equivalent or less of the metal hydroxide, relative to γ-butyrolactone, is added to maintain an average molar equivalence, and preferably a slight deficiency, of the metal hydroxide, similar to the continuous process discussed above. This provides a resulting product solution of γ-hydroxybutyrate having a pH of about 8 or less, preferably from about 6 to about 8, and more preferably from about 7 to about 8, upon reaching equilibrium. The batch process does not require and typically does not involve a pH adjustment or acid/base addition, subsequent to the preparation of the aqueous γ-hydroxybutyrate, to achieve the desired pH range.

After forming the product solution of γ-hydroxybutyrate, the product solution is equilibrated if desired at room temperature or at higher temperatures. The product solution is further optionally processed through a concentrating process, such as the process discussed with reference to FIG. 3, or another concentrating or drying process. As discussed above, the residence time and/or heat used during the concentrating process can be used to drive the product solution to final equilibrium.

The aqueous concentrate of γ-hydroxybutyrate is analyzed using techniques such as HPLC or GC/GC-MS. For example, purity analysis can be accomplished by the removal of water from the aqueous concentrate by lyophilization or azeotrope with isopropanol, as discussed above, to obtain a dry solid. The trimethylsilyl (TMS) derivative of the dry γ-hydroxybutyrate is then formed and analyzed by GC or GCMS.

The processes described above are also useful for preparing other hydroxy-carboxylates from the corresponding lactones, according to the following scheme:

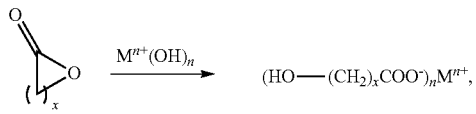

wherein x is an integer ranging from 1 to 6; wherein n is an integer ranging from 1 to 3; and wherein M is a metal, including any of the metals discussed above (e.g., alkali metals, alkali earth metals, transition metals, etc.).

The following examples are provided as illustrative of the present invention and not limitative thereof.

EXAMPLE 1

The continuous process procedure described below is used to prepare a five kilogram sample of sodium γ-hydroxybutyrate as an aqueous concentrate.

The following solutions are prepared as feedstock for the continuous reactor: γ-butyrolactone feedstock solution—γ-butyrolactone (3.4 kg, about 3.0 L, 39.4 mol) is diluted with 3.0 L of reagent grade water and mixed until homogeneous (clear, colorless) resulting in a 6.56 M solution of γ-butyrolactone in water; NaOH feedstock solution—NaOH (49 wt % in $H_2O$, 3.2 kg, about 2.1 L, 39.4 mol, 1.0 equivalent relative to γ-butyrolactone) is diluted with 4.2 L of reagent grade water, mixed until homogeneous (clear, colorless), and allowed to cool to room temperature, resulting in a 6.56 M solution of NaOH in water. The headspace above both feedstock solutions is kept inert under a blanket of nitrogen during preparation and reaction.

Each solution is fed by peristaltic pump through separate jacketed ($T_{jacket}$=~0° C.) static mixers (316SS, 21 alternating split-helical mixing elements, 0.25" OD×0.194" ID×11.50" L) to pre-cool the feed solutions prior to mixing. The aqueous γ-butyrolactone solution is fed at a set flow rate of about 52.0 mL/min, while the aqueous NaOH solution is fed at a slightly lower flow rate of about 49.5 mL/min. The two pre-cooled feed solutions are combined through a union and fed concurrently into two jacketed static mixers (316SS, 32 alternating split-helical mixing elements, 0.50" OD×0.43" ID×24.75" L) in series at a total combined feed rate of about 101.5 mL/min. As the two feed solutions are of equivalent concentration, these flow rates result in a reaction ratio of 0.95 equivalents of NaOH relative to γ-butyrolactone in the reactor. The fluid in the first reactor jacket in the series is maintained at 25° C.±2.5° C. (concurrent flow) while the fluid in the second is maintained at 55° C.±2.5° C. (countercurrent flow). For the reactor and reaction conditions described above, the pH of process stream immediately after the first jacketed reactor is typically 12±0.5 at a temperature of 40±2.5° C., while the pH of the process stream immediately after the second jacketed reactor is typically 10±1.0 at a temperature of 47.5±2.5° C. The intimately mixed solutions from the outlet of the reactor are fed through a tube (polypropylene, 0.25" OD, 0.125" ID) and collected in a receiving vessel. The headspace above the product solution is kept inert under a blanket of nitrogen during and after the reaction. The pH of the resulting clear, colorless to straw yellow solution, at equilibrium, is typically 7.3±0.1.

The relative ratio of the reagants in the reaction zone in this Example is determined by the following calculation, using equations (1) and (2) discussed above.

$$\text{NaOH flow rate(mol/min)} = \frac{6.56 \text{ mol}/L \times 49.5 \text{ mL/min}}{1000 \text{ mL/min}} = 0.3247 \text{ mol/min} \quad (1)$$

$$\text{GBL flow rate(mol/min)} = \frac{6.56 \text{ mol}/L \times 52.0 \text{ mL/min}}{1000 \text{ mL/min}} = 0.3411 \text{ mol/min} \quad (1)$$

$$\frac{\text{NaOH flow rate(mol/min)}}{\text{GBL flow rate(mol/min)}} = \frac{0.3247 \text{ mol/min}}{0.3411 \text{ mol/min}} = 0.95 \text{ equiv. NaOH vs. GBL} \quad (2)$$

The solution is then concentrated in vacuo using a Wiped-Film Evaporator (WFE) to a sodium γ-hydroxybutyrate aqueous concentrate of about 40 wt % to about 55 wt %. The headspace above the feed and product solutions for the WFE are kept inert under a blanket of nitrogen during concentration.

The sodium γ-hydroxybutyrate aqueous concentrate is then filtered (10-20 micron filter) and packaged. The headspace above the feed and product solutions for the filtration and packaging operations are kept inert under a blanket of nitrogen. After concentration, the pH of the solution is typically 7.7±0.1 (upon reaching equilibrium). In this instance, equilibrium is reaching during the concentration process. The resulting aqueous concentrate meets or exceeds 99% purity as measured by GC analysis of the bis-TMS (trimethylsilyl) derivative of the final product.

Alternatively, the output of the continuous reactor is fed directly, or via a surge tank, into the concentration equipment (e.g., WFE), and filtered/packaged upon exiting the WFE, resulting in continuous production of neutral pH sodium γ-hydroxybutyrate aqueous concentrate from start to finish.

The process described above can also be used to prepare aqueous solutions of higher or lower sodium γ-hydroxybutyrate content without the need for removal of water, as further demonstrated in Example 2.

EXAMPLE 2

The continuous process procedure described below is used to prepare a five kilogram sample of sodium γ-hydroxybutyrate as an aqueous concentrate at about 42 wt %.

The following solutions are prepared as feedstock for the continuous reactor: γ-butyrolactone feedstock solution—γ-butyrolactone (3.4 kg, about 3.0 L, 39.4 mol) is diluted with 2.2 L of reagent grade water and mixed until homogeneous (clear, colorless); NaOH feedstock solution—NaOH (49 wt % in $H_2O$, 3.2 kg, about 2.1 L, 39.4 mol, 1.0 equivalent relative to γ-butyrolactone) is diluted with 3.0 L of reagent grade water, mixed until homogeneous (clear, colorless), and allowed to cool to room temperature. The headspace above both solutions is kept inert under a blanket of nitrogen during preparation and reaction.

Each solution is fed by peristaltic pump through separate jacketed ($T_{jacket}$=~0° C.) static mixers (316SS, 21 alternating split-helical mixing elements, 0.25" OD×0.194" ID×11.50" L) to pre-cool the feed solutions prior to mixing. The aqueous GBL solution is fed at a set flow rate of about 52.0 mL/min, while the aqueous NaOH solution is fed at slightly lower flow rate of about 49.5 mL/min. The two pre-cooled feed solutions are then combined through a union and fed concurrently into two jacketed static mixers (316SS, 32 alternating split-helical mixing elements, 0.50" OD×0.43" ID×24.75" L) in series at a total combined feed rate of about 101.5 mL/min. As the two feed solutions are of equivalent concentration, these flow rates result in a reaction ratio of 0.95 equivalents of NaOH relative to γ-butyrolactone in the reactor. The first reactor jacket in the series is set at 25° C. (concurrent flow), while the second is set at 55° C. (countercurrent flow). The intimately mixed solutions from the outlet of the reactor is then fed through a tube (PP, 0.25" OD, 0.125" ID) and collected in a receiving vessel. The headspace above the product solution is kept inert under a blanket of nitrogen during and after the reaction.

This resulting solution is allowed to equilibrate before being filtered (15-20 micron filter) and packaged. The headspace above the feed and product solutions for the filtration and packaging operations are kept inert under a blanket of nitrogen. The pH of the resulting clear, colorless to straw yellow solution at equilibrium is typically 7.5±0.1. The resulting aqueous concentrate meets or exceeds 99% purity as measured by GC analysis of the bis-TMS (trimethylsilane) derivative of the final product. The aqueous concentrate produced is prepared at the desired concentration of about 42 wt % and does not require further concentration.

EXAMPLE 3

The batchwise procedure described below is used to prepare a five-kilogram sample of sodium γ-hydroxybutyrate as an aqueous concentrate.

The following solutions are prepared as feedstock for the batchwise production of sodium γ-hydroxybutyrate: aqueous γ-butyrolactone solution—γ-butyrolactone (3.4 kg, about 3.0 L, 39.4 mol) is diluted with 3.0 L of reagent grade water and mixed until homogeneous (clear, colorless) resulting in a 6.56 M solution of γ-butyrolactone in water; aqueous NaOH solution—NaOH (49 wt % in $H_2O$, 3.0 kg, about 2.0 L, 37.4 mol, 0.95 equivalents relative to γ-butyrolactone) is diluted with 4.0 L of reagent grade water, mixed until homogeneous (clear, colorless), and allowed to cool to room temperature, resulting in a 6.56 M solution of NaOH in water. The headspace above both solutions is kept inert under a blanket of nitrogen during preparation and reaction.

The aqueous γ-butyrolactone solution is prepared in a 15-L jacketed glass reactor with agitation under an inert (nitrogen) atmosphere. The aqueous NaOH solution is added to the reactor slowly over a period of 2 hours, maintaining the reaction temperature at 50 to 60° C. by controlling the jacket temperature (set at 55±5° C.) and the NaOH solution addition rate. Once the addition is complete, the resulting clear, colorless to straw-yellow mixture is allowed to equilibrate with stirring under an inert (nitrogen) atmosphere prior to further processing.

The pH of the resulting solution is typically 7.3±0.1 (upon reaching equilibrium) prior to concentration. The solution is concentrated in vacuo using a Wiped-Film Evaporator (WFE) to a sodium γ-hydroxybutyrate aqueous concentrate of about 40 wt % to about 65 wt %. The headspace above the feed and product solutions for the WFE are kept inert under a blanket of nitrogen during concentration.

The sodium γ-hydroxybutyrate aqueous concentrate is filtered (15-20 micron filter) and packaged. The headspace above the feed and product solutions for the filtration and packaging operations are kept inert under a blanket of nitrogen. After concentration, the pH of the solution is typically 7.7±0.1 (upon reaching equilibrium). The resulting aqueous concentrate meets or exceeds 99% purity as measured by GC analysis of the bis-TMS (trimethylsilane) derivative of the final product.

The process described above is also used to prepare aqueous solutions of higher or lower sodium γ-hydroxybutyrate content without the need for removal of water, as further demonstrated in Example 4.

EXAMPLE 4

The batchwise procedure described below is used to prepare a five-kilogram sample of sodium γ-hydroxybutyrate as an aqueous concentrate at about 42 wt %.

The following solutions are prepared as feedstock for the batchwise production of sodium γ-hydroxybutyrate: aqueous γ-butyrolactone solution—γ-butyrolactone (3.4 kg, about 3.0 L, 39.4 mol) is diluted with 2.2 L of reagent grade water and mixed until homogeneous (clear, colorless); aqueous NaOH solution—NaOH (49 wt % in $H_2O$, 3.0 kg, about 2.0 L, 37.4 mol, 0.95 equivalents relative to γ-butyrolactone) is diluted with 2.9 L of reagent grade water, mixed until homogeneous (clear, colorless), and allowed to cool to RT. The headspace of both solutions is kept inert under a blanket of nitrogen during preparation and reaction.

The aqueous γ-butyrolactone solution is prepared in a 15-L jacketed glass reactor with agitation under an inert (nitrogen) atmosphere. The aqueous NaOH solution is added to the reactor slowly over a period of 2 hours, maintaining the reaction temperature at 50 to 60° C. by controlling the jacket temperature (set at 55±5° C.) and the NaOH solution addition rate. Once the addition is complete, the resulting clear, colorless to straw yellow mixture is allowed to equilibrate with stirring under an inert (nitrogen) atmosphere prior to further processing.

The sodium γ-hydroxybutyrate aqueous concentrate is filtered (15-20 micron filter) and packaged. The headspace above the feed and product solutions for the filtration and packaging operations are kept inert under a blanket of nitrogen. The pH of the resulting solution is typically 7.5±0.1 (upon reaching equilibrium). The resulting aqueous concentrate meets or exceeds 99% purity as measured by GC analysis of the bis-TMS (trimethylsilane) derivative of the final product. The aqueous concentrate produced is prepared at the desired concentration of about 42 wt % and does not require further concentration.

What is claimed is:

1. A continuous process for preparing γ-hydroxybutyrate, the process comprising:
   (a) continuously feeding a first feedstock of γ-butyrolactone and a second feedstock of aqueous metal hydroxide into a reaction zone, at relative rates sufficient to maintain about 1 equivalent or less of metal hydroxide, relative to γ-butyrolactone, in the reaction zone;
   (b) continuously reacting the γ-butyrolactone and the metal hydroxide in the reaction zone to form aqueous γ-hydroxybutyrate; and
   (c) continuously discharging the aqueous γ-hydroxybutyrate from the reaction zone.

2. The process of claim 1, wherein the first and second feedstocks are fed at relative rates sufficient to maintain less than 1 equivalent of metal hydroxide, relative to γ-butyrolactone, in the reaction zone.

3. The process of claim 1, wherein the reaction zone is maintained at 100° C. or less.

4. The process of claim 1, wherein the reaction zone is maintained at 65° C. or less.

5. The process of claim 1, further comprising: concentrating the aqueous γ-hydroxybutyrate.

6. The process of claim 5, wherein concentrating is carried out by wiped film evaporation.

7. The process of claim 1, wherein the aqueous γ-hydroxybutyrate has a pH of about 8 or less, upon reaching equilibrium.

8. The process of claim 1, wherein the aqueous γ-hydroxybutyrate has a pH of from about 6 to about 8, upon reaching equilibrium.

9. The process of claim 1, wherein the aqueous γ-hydroxybutyrate has a pH of from about 7 to about 8, upon reaching equilibrium.

10. The process of claim 1, wherein at least one of the first or second feedstock is pre-cooled prior to being fed into the reaction zone.

11. The process of claim 10, wherein at least one of the first or second feedstock is pre-cooled by passing the feedstock through a jacketed static mixer having a jacket temperature of about 0° C.

12. The process of claim 1, wherein the reaction zone comprises a first jacketed static mixer and a second jacketed static mixer downstream of the first mixer; the first jacketed static mixer having a jacket temperature of from about 15° C. to about 35° C., and the second jacketed static mixer having a jacket temperature of from about 45° C. to about 65° C.

13. The process of claim 12, wherein the pH of the reaction mixture, immediately after passing through the first jacketed static mixer is from 11.5 to 12.5, at a temperature of from 37.5 to 42.5° C.

14. The process of claim 12, wherein the pH of the reaction mixture, immediately after passing through the second jacketed static mixer is from 9 to 11, at a temperature of from 45 to 50° C.

15. The process of claim 1, wherein the metal hydroxide is an alkali metal hydroxide.

16. The process of claim 1, wherein the metal hydroxide is sodium hydroxide.

17. A continuous process for preparing γ-hydroxybutyrate, the process comprising:
   (a) continuously feeding a first feedstock of γ-butyrolactone and a second feedstock of aqueous metal hydroxide containing about 1 equivalent or less of metal hydroxide, relative to γ-butyrolactone, into a reaction zone;
   (b) continuously reacting the γ-butyrolactone and the metal hydroxide in the reaction zone to form aqueous γ-hydroxybutyrate; and
   (c) continuously discharging the aqueous γ-hydroxybutyrate from the reaction zone.

18. The process of claim 17, wherein the first and second feedstocks are fed into the reaction zone at relative rates sufficient to maintain about 1 equivalent or less of metal hydroxide, relative to γ-butyrolactone, in the reaction zone.

19. The process of claim 17, wherein the first and second feedstocks are fed into the reaction zone at relative rates sufficient to maintain less than 1 equivalent of metal hydroxide, relative to γ-butyrolactone, in the reaction zone.

20. The process of claim 17, wherein the reaction zone is maintained at 100° C. or less.

21. The process of claim 17, wherein the reaction zone is maintained at 65° C. or less.

22. The process of claim 17, further comprising: concentrating the aqueous γ-hydroxybutyrate.

23. The process of claim 22, wherein concentrating is carried out by wiped film evaporation.

24. The process of claim 17, wherein the aqueous γ-hydroxybutyrate has a pH of about 8 or less, upon reaching equilibrium.

25. The process of claim 17, wherein the aqueous γ-hydroxybutyrate has a pH of from about 6 to about 8, upon reaching equilibrium.

26. The process of claim 17, wherein the aqueous γ-hydroxybutyrate has a pH of from about 7 to about 8, upon reaching equilibrium.

27. The process of claim 17, wherein at least one of the first or second feedstock is pre-cooled prior to being fed into the reaction zone.

28. The process of claim 27, wherein at least one of the first or second feedstock is pre-cooled by passing the feedstock through a jacketed static mixer having a jacket temperature of about 0° C.

29. The process of claim 17, wherein the reaction zone comprises a first jacketed static mixer and a second jacketed static mixer downstream of the first mixer; the first jacketed static mixer having a jacket temperature of from about 15° C. to about 35° C., and the second jacketed static mixer having a jacket temperature of from about 45° C. to about 65° C.

30. The process of claim 29, wherein the pH of the reaction mixture, immediately after passing through the first jacketed static mixer is from 11.5 to 12.5, at a temperature of from 37.5 to 42.5° C.

31. The process of claim 29, wherein the pH of the reaction mixture, immediately after passing through the second jacketed static mixer is from 9 to 11, at a temperature of from 45 to 50° C.

32. The process of claim 17, wherein the metal hydroxide is an alkali metal hydroxide.

33. The process of claim 17, wherein the alkali metal hydroxide is sodium hydroxide.

* * * * *